US009242263B1

(12) United States Patent
Copeman et al.

(10) Patent No.: US 9,242,263 B1
(45) Date of Patent: Jan. 26, 2016

(54) DYNAMIC ULTRASONIC GENERATOR FOR ULTRASONIC SPRAY SYSTEMS

(71) Applicant: Sono-Tek Corporation, Milton, NY (US)

(72) Inventors: Randy A. Copeman, Glenford, NY (US); Vincent D. Whipple, Kingston, NY (US); Harvey L. Berger, Hyde Park, NY (US); Matthew C. Walls, Highland Mills, NY (US); Robb W. Engle, Kingston, NY (US)

(73) Assignee: Sono-Tek Corporation, Milton, NY (US)

( * ) Notice: Subject to any disclaimer, the term of this patent is extended or adjusted under 35 U.S.C. 154(b) by 21 days.

(21) Appl. No.: 14/217,922

(22) Filed: Mar. 18, 2014

Related U.S. Application Data

(60) Provisional application No. 61/793,970, filed on Mar. 15, 2013.

(51) Int. Cl.
*A61M 11/06* (2006.01)
*B05B 17/06* (2006.01)

(52) U.S. Cl.
CPC .................................. *B05B 17/0653* (2013.01)

(58) Field of Classification Search
CPC ............ B05B 17/0615; B05B 17/0646; B05B 17/0684; B01D 1/20
USPC .................... 239/102.2, 102.1, 133, 134, 338
See application file for complete search history.

(56) References Cited

U.S. PATENT DOCUMENTS

| | | | | |
|---|---|---|---|---|
| 4,642,581 | A | 2/1987 | Erickson | |
| 4,659,014 | A * | 4/1987 | Soth et al. | 239/102.2 |
| 4,901,034 | A * | 2/1990 | Frank-Peter | B05B 17/0607 239/102.2 |
| 4,973,876 | A * | 11/1990 | Roberts | B06B 1/0253 310/316.01 |
| 5,588,592 | A * | 12/1996 | Wilson | 239/4 |
| 6,122,223 | A * | 9/2000 | Hossack | 367/11 |
| 6,383,815 | B1 * | 5/2002 | Potyrailo | 436/2 |
| 7,247,346 | B1 * | 7/2007 | Sager et al. | 427/162 |
| 2003/0145849 | A1 * | 8/2003 | Drinan | A61B 5/411 128/200.14 |
| 2011/0101536 | A1 * | 5/2011 | Chiang et al. | 257/773 |

* cited by examiner

*Primary Examiner* — Davis Hwu
(74) *Attorney, Agent, or Firm* — Miles & Stockbridge PC

(57) ABSTRACT

An ultrasonic generator is provided. The ultrasonic generator includes an amplifier for outputting a drive signal to an ultrasonic atomizing nozzle, and a microcontroller, coupled to the amplifier, to control an output power of the amplifier. The microcontroller includes a load leveling operating mode in which the output power of the amplifier fluctuates to match changing load conditions of the ultrasonic atomizing nozzle.

21 Claims, 5 Drawing Sheets

DYNAMIC ULTRASONIC GENERATOR FOR ULTRASONIC SPRAY SYSTEMS

CROSS-REFERENCE TO RELATED APPLICATIONS

This application is a Nonprovisional of U.S. Provisional Patent Application Ser. No. 61/793,970, filed on Mar. 15, 2013, the disclosure of which is incorporated herein by reference in its entirety.

TECHNICAL FIELD

This application generally relates to ultrasonic spraying, and more particularly relates to a dynamic ultrasonic generator for ultrasonic spray systems.

BACKGROUND

An ultrasonic atomizer nozzle can change a stream of liquid to a plume of dispersed droplets, whose sizes are significantly uniform and whose kinetic energy are at a minimum. The droplet size is based on the resonant frequency of the nozzle and certain properties of the liquid such as surface tension and density. The minimal kinetic energy of the atomized plume results from the droplets falling off the tops of liquid waves in a film that is formed at an anti-node or distal end of the nozzle. This is done through the use of a uniquely shaped horn designed to achieve a target resonate frequency, the use of piezo-electric transducers configured to convert the input of an alternating or time-varying signal to a mechanical resonance in the subassembly, and a means for connecting the driving signal to the transducers, generally through one or more electrodes.

Atomization occurs at the lowest power levels when the frequency of the driving signal matches the nozzle's natural resonant frequency. Required power levels are significantly affected by many conditions, such as, for example, introduction of liquid to the flow channel and to the atomizing surface, the mass of that liquid and its viscosity, changes in temperature of the materials in the complex subassembly that change the wavelength of the material and, therefore, the resonant frequency, accumulation of foreign materials such as dirt or spray residue on the nozzle's front horn stem or other active horn surface, etc.

Traditionally, a constant power is delivered by an ultrasonic generator to the nozzle from analog electronic driving circuits. These analog driving circuits require time to obtain frequency lock to the nozzle, which may require 500 milliseconds or longer. As such, these ultrasonic generators cannot dynamically react to changing load conditions of the nozzle, such as, for example, impedance, frequency, etc., in a manner that is both fast and stable while providing optimal atomization performance.

Therefore a need exists for a dynamic ultrasound generator for ultrasonic spray systems that quickly and accurately adjusts for different nozzle load conditions using programmable digital circuits.

SUMMARY

Embodiments of the present invention advantageously provide an ultrasonic generator that includes an amplifier for outputting a drive signal to an ultrasonic atomizing nozzle, and a microcontroller, coupled to the amplifier, to control an output power of the amplifier. The microcontroller includes a load leveling operating mode in which the output power of the amplifier fluctuates to match changing load conditions of the ultrasonic atomizing nozzle.

There has thus been outlined, rather broadly, certain embodiments of the invention in order that the detailed description thereof herein may be better understood, and in order that the present contribution to the art may be better appreciated.

Before explaining at least one embodiment of the invention in detail below, it is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

DETAILED DESCRIPTION

Figure 1:
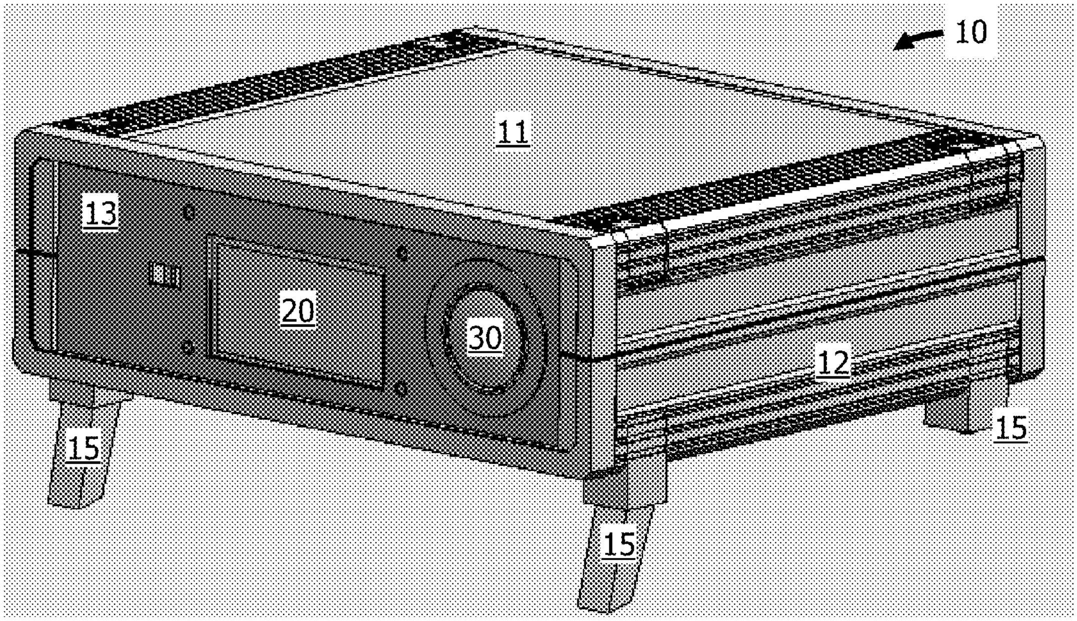
FIG. 1 is a perspective view of a dynamic ultrasonic generator, in accordance with an embodiment of the present invention.

The invention will now be described with reference to the drawing figures, in which like reference numerals refer to like parts throughout.

Embodiments of the present invention provide a dynamic ultrasonic generator 10 that drives piezoelectric transducers in a complex resonating subassembly, such as an ultrasonic atomizing nozzle, in the ultrasonic frequency range between about 20 kHz and about 3 MHz to cause atomization of liquid. The dynamic ultrasonic generator 10 operates in one or more modes according to the spray process, adjusts the frequency of the ultrasonic atomizing nozzle drive signal to the characteristics of the driven ultrasonic atomizing nozzle while simultaneously allowing the voltage and current components of the ultrasonic drive signal to be out of phase, leading or lagging, and dynamically and automatically switches to a separate, higher potential output range when the impedance of the ultrasonic atomizing nozzle load exceeds a predetermined threshold value. The dynamic ultrasonic generator 10 advantageously provides great variability without requiring specialized circuits for each unique ultrasonic atomizer load.

Figure 2:
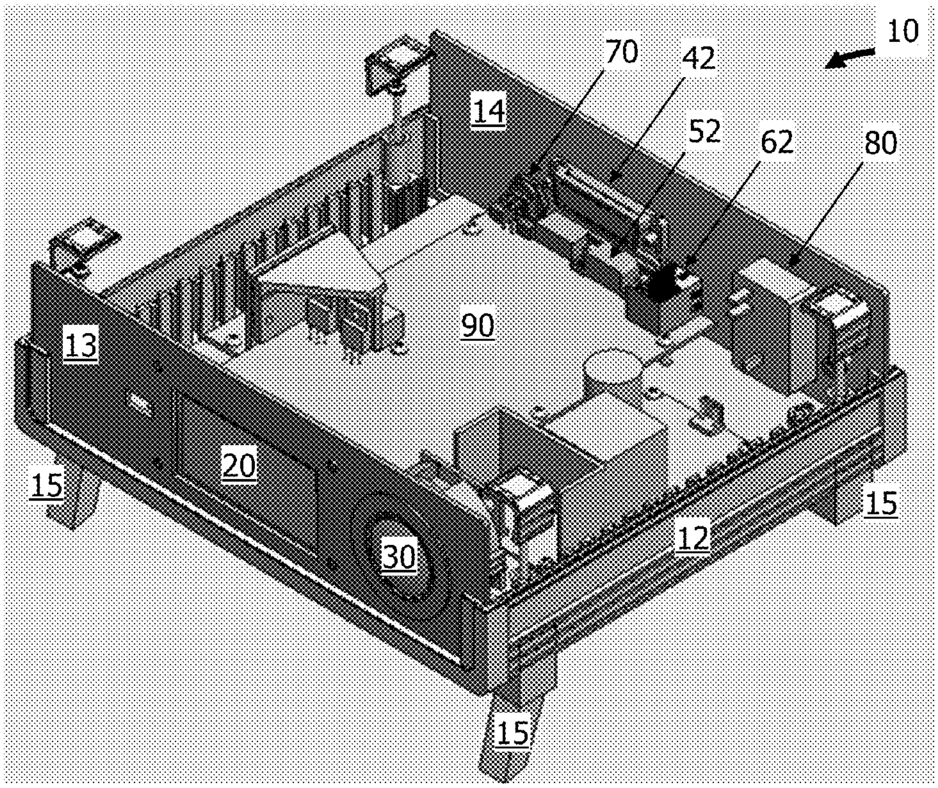
FIG. 2 is a perspective view of the dynamic ultrasonic generator depicted in FIG. 1 with the upper housing removed, in accordance with an embodiment of the present invention.

FIGS. 1 and 2 are perspective views of a dynamic ultrasonic generator 10, in accordance with an embodiment of the present invention. The dynamic ultrasonic generator 10 includes a housing in which one or more circuit boards, power conversion components, interface components, etc., are disposed. In one embodiment, the housing includes an upper portion 11, a lower portion 12, a front portion or panel 13 and a rear portion or panel 14. Supports 15 may depend from the lower housing 12; alternatively, a mechanical interface, such as a rail, may be attached to, or incorporated within, the housing for installation within an equipment rack. The front panel 13 includes a display 20, such as a backlit graphic LCD display (depicted), a touchscreen display, etc., as well as user interface (I/F) controls 30, such as an illuminated rotary wheel encoder (depicted), a touchpad, a keypad, buttons arranged around the perimeter of the display 20, an on/off button, etc. The display 20 presents information through a graphical user interface, or, alternatively, the display 20 may incorporate a touchscreen to accept user input. The illuminated rotary wheel encoder may convey status through different colors, such as, for example, red to indicate that the dynamic ultrasonic generator 10 is off and/or not ready, amber to indicate alarms and/or warnings, green to indicate that the dynamic ultrasonic generator 10 is on and/or ready, blue to indicate that the dynamic ultrasonic generator 10 is triggered, etc.

FIG. 2 depicts the dynamic ultrasonic generator 10 with the top housing cover 11 removed. Generally, circuit board 90 supports various electronic components described in detail below. Rear panel 14 supports various connection, including, for example, a connector 42 for a general I/O interface 40, a connector 52 for a serial communications interface 50, a connector 62 for an Ethernet communications interface 60, a nozzle drive power connector 70, an A/C power connector 80, etc. General I/O interface 40 may include, for example, an external trigger input, external level control input, external alarm output, digital inputs, digital outputs, analog inputs, analog outputs, etc. In one embodiment, the I/O interface connector 42 is a 25-pin female D-SUB connector, the serial communications interface connector 52 is a male DB-9 connector, the Ethernet communications interface connector 62 is an RJ45 connector, and the nozzle drive power connector 70 is a female M12 connector.

Figure 3:
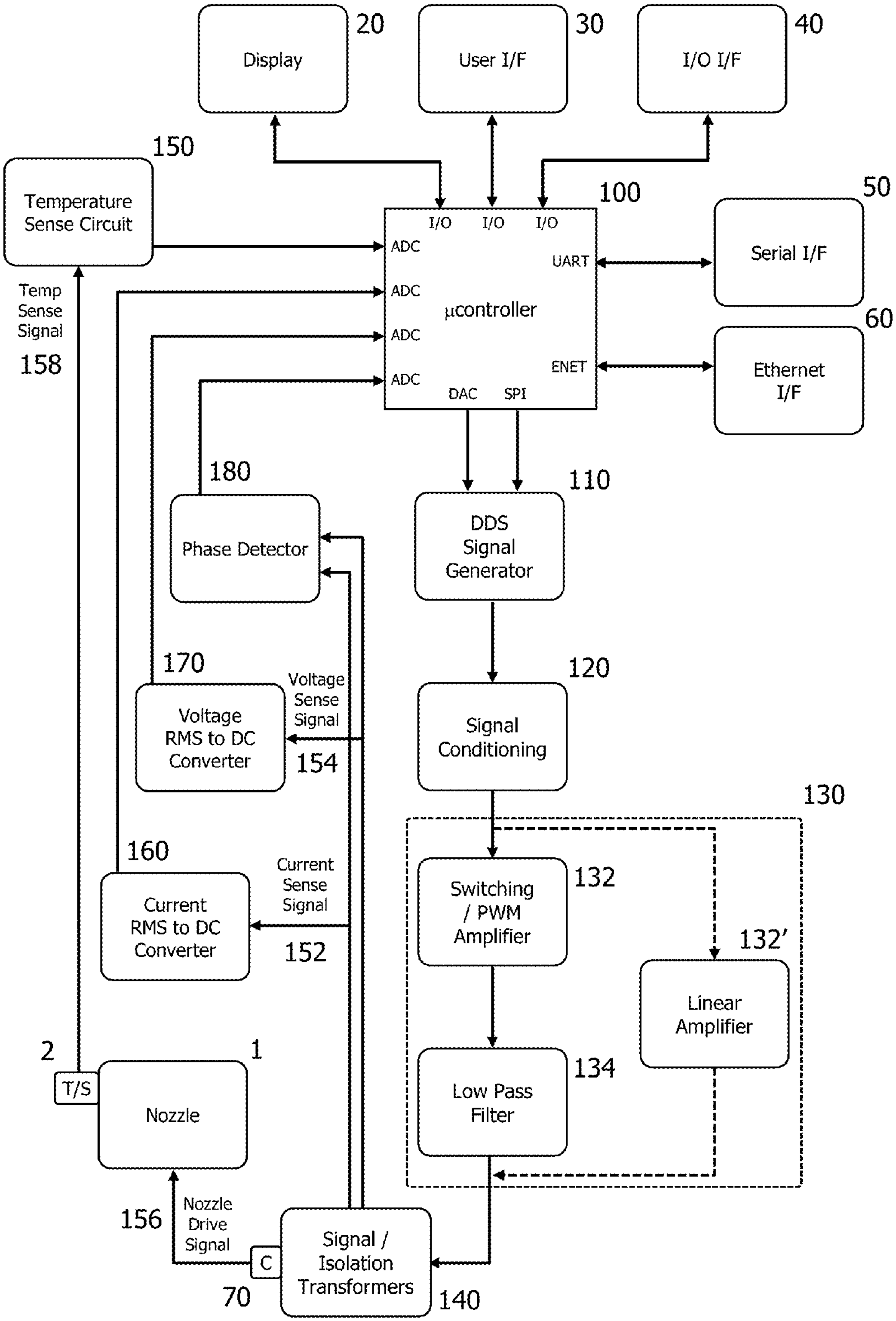
FIG. 3 is system block diagram of a dynamic ultrasonic generator, in accordance with an embodiment of the present invention.
Figure 4:
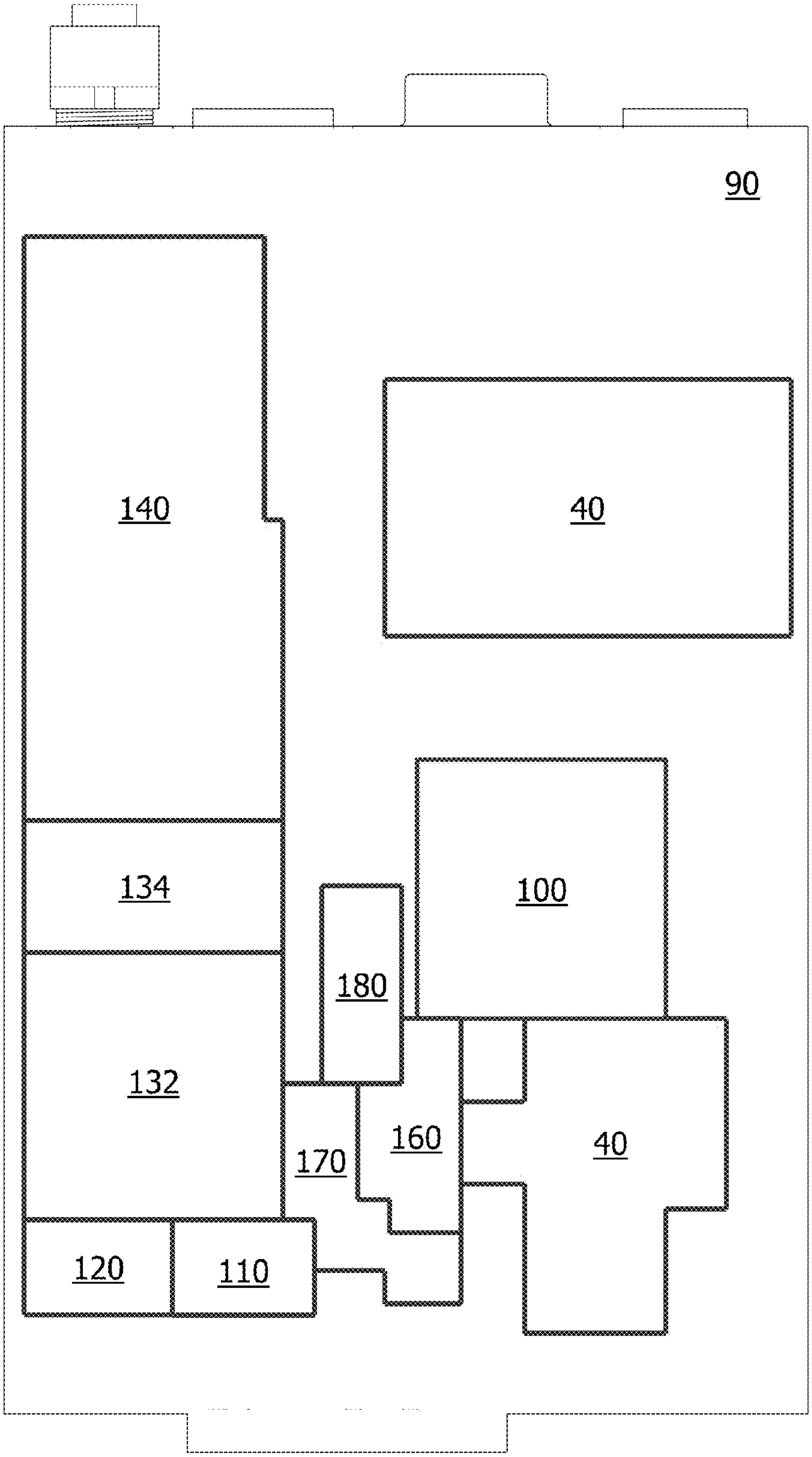
FIGS. 4 and 5 depict a general physical arrangement of several components on the top and bottom surfaces of a circuit board for a dynamic ultrasonic generator, respectively, in accordance with an embodiment of the present invention.
Figure 5:
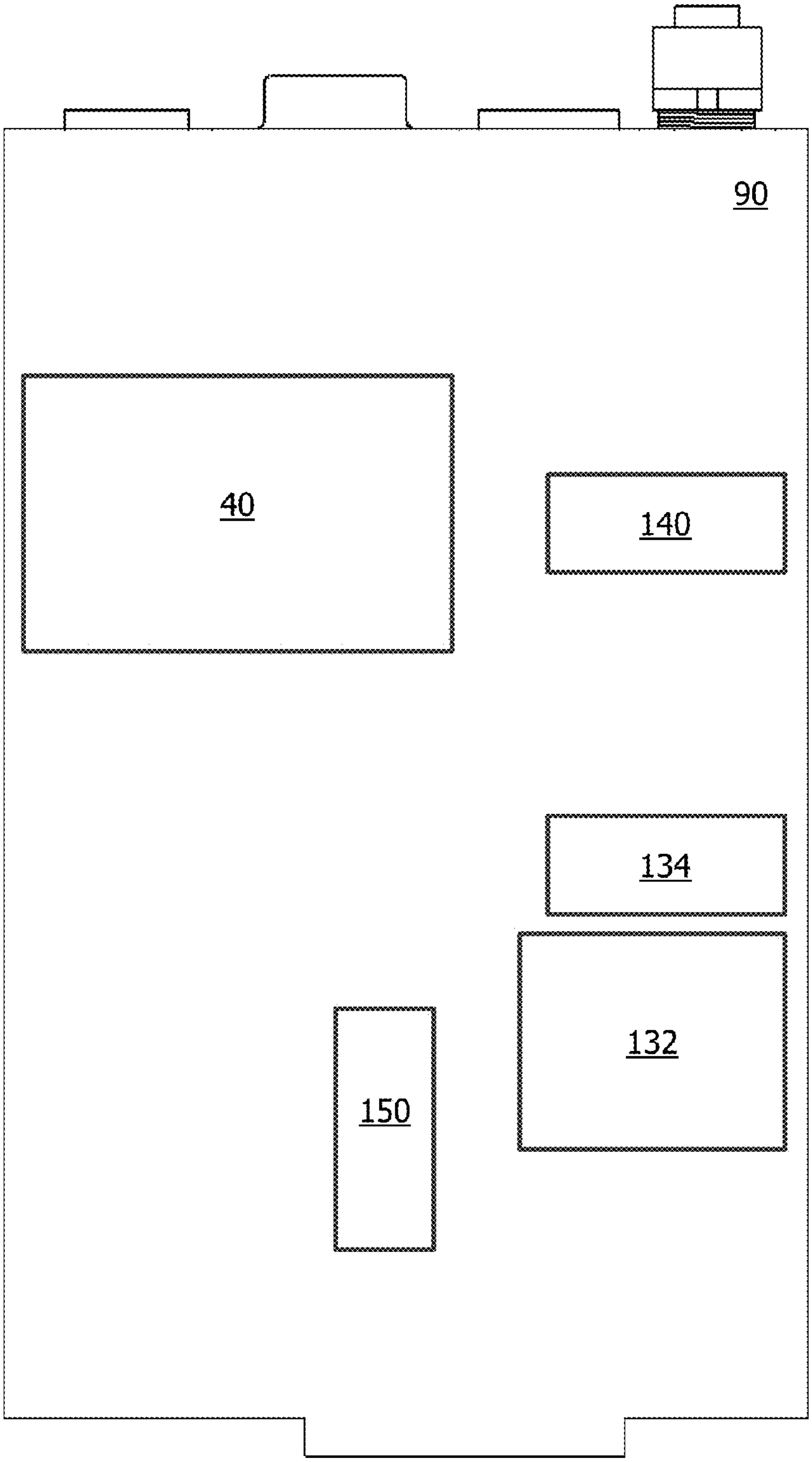

FIG. 3 is system block diagram of a dynamic ultrasonic generator 10, in accordance with an embodiment of the present invention. FIGS. 4 and 5 depict a general physical arrangement of several components on the top and bottom surfaces of circuit board 90, respectively, in accordance with an embodiment of the present invention.

Microcontroller 100 is the heart of the dynamic ultrasonic generator 10, and includes a central processing unit (CPU) or microprocessor, and one or more internal buses to couple the microprocessor to volatile and/or non-volatile memory, and to various I/O peripheral modules, such as analog to digital converters (ADCs), digital to analog convertors (DACs), serial peripheral interfaces (SPIs), analog and digital I/O ports, serial communications modules, Ethernet communications modules, etc. In the embodiment depicted in FIG. 3, microcontroller 100 is coupled to the display 20, user interface 30 and I/O interface 40 via respective I/O ports, to the serial communications interface 50 via a UART port, and to the Ethernet communications interface 60 via an Ethernet port.

Accordingly, in addition to controlling the ultrasonic atomizing nozzle drive signal, microcontroller 100 may also advantageously control other elements of the spray process, such as, for example, solenoids, pumps, regulators, etc., using these digital and analog inputs and outputs. In these embodiments, microcontroller 100 reads the digital inputs and digitizes the analog input elements, manipulates the digitized data, and updates the associated digital and analog process elements to provide greater process control and timing between all of the ultrasonic spray process elements and associated devices. Spray process data may be communicated to the microcontroller 100 via various communication protocols, such as RS232/485, Ethernet, etc., and microcontroller 100 can provide process timing in combination with specific ultrasonic atomizing nozzle control signals. Advantageously, the dynamic ultrasonic generator 10 can obtain frequency lock in less than 10 milliseconds, which is critical for high-speed, high-precision spraying applications.

Microcontroller 100 is coupled to a direct digital synthesis (DDS) signal generator 110, such as, for example, Analog Devices AD9838, via DAC and SPI ports. The DDS signal generator 110 is coupled to an output amplifier 130 through a signal conditioning circuit 120. In one embodiment, the output amplifier 130 is a switching/pulse width modulated (PWM) amplifier 132 with a low pass filter 134 coupled to the output, while in another embodiment, the output amplifier 130 is a linear amplifier 132'. The output amplifier 130 is coupled to signal/isolation transformers 140, which provide the nozzle drive signal to nozzle 1 over the nozzle drive power connector 70 and nozzle drive signal 156. A current sense signal 152 and a voltage sense signal 154 are simultaneously provided to a current level detector circuit 160, a voltage level detector circuit 170, and a phase detector circuit 180 by the signal/isolation transformers 140. The outputs of these components are provided to respective ADC ports on the microcontroller 100.

In certain embodiments, a temperature sensor 2 may be attached to the ultrasonic atomizing nozzle 1, and analog temperature signals may be provided to a temperature sense circuit 150, which is coupled to an ADC port on the microcontroller 100. Alternatively, a digital temperature sensor may be used, in which case digital temperature data may be provided to the temperature sense circuit 150, or alternatively, provided directly to an I/O or UART port on microcontroller 100. Temperature data signals may be provided over temperature cable 158.

The temperature sense circuit 150 is configured to work with, but not limited to, temperature sensors 2 that change in electrical resistance in relation to the applied temperature. A constant current is sent through the temperature sensor 2 to produce a voltage across the sensor resistive element that is proportional to the applied temperature. This voltage is then amplified to match the signal levels of the respective ADC of the microcontroller 100. The microcontroller 100 reads this voltage periodically, typically greater several times per second, and then responds to the measured temperature. For example, if an over-temperature condition is detected, the microcontroller 100 may reduce the magnitude of the ultrasonic atomizer nozzle driving signal in order to lower the temperature of the ultrasonic atomizer nozzle 1. In this example, the magnitude may be zeroed as well. In another example, if a specific atomizer nozzle temperature is desired, the microcontroller 100 may increase or decrease the ultrasonic atomizer nozzle driving signal, as necessary, to maintain the desired atomizer nozzle temperature. Temperature sensors 2 with a sensor resistive element in the range of tens to hundreds of ohms may be used. Faults, such as short circuits and open circuits, for example, may also be detected within the temperature sensor 2.

The DDS signal generator 110 generates the core sine-waves that are provided to the signal conditioning circuits 120. The frequencies of the two generated sine-waves match the resonant frequency of the ultrasonic atomizer nozzle 1, where the two generated sine-wave signals are 180° out of phase with respect to each other. After reading and processing the output signal level and phase data of the nozzle drive power signal, via the current level detector circuit 160, the voltage level detector circuit 170, and the phase detector circuit 180, microcontroller 100 sends a new frequency control word, via the SPI port, to the DDS signal generator 110. Simultaneously, the microcontroller 100 also updates the signal level of the DDS signal generator 110, via the DAC port, connected to the signal level control input of the DDS signal generator 110. In one embodiment, this DAC port provides 12-bit resolution.

The signal conditioning circuit 120 amplifies the sine-wave signals generated by the DDS signal generator 110 to levels required by the input stage of the output amplifier 130, which may be the modulator of the switching/PWM amplifier 132 or the first stage of the linear amplifier 132'. In one embodiment, high-speed, low-distortion operational amplifiers, such as, for example, Texas Instruments OPA2365A, are used to perform the amplifying function.

The switching/PWM amplifier 132 may be described as including three main sections: the modulator, the driving stage and the power output stage.

The modulator may include two high-speed comparators with high-speed logic-level totem-pole outputs, such as, for example, Texas Instruments LMV7219, which are coupled to the inputs of the output driving stage. The two, 180° out of phase, conditioned, sine-wave signals, produced by the signal conditioning circuit 120, are then coupled to separate comparators, one for each sine-wave signal. A sampling signal, in the form of, but not limited to, a triangle waveform is coupled to the second input of each comparator in the modulator stage. A signal with a constant period and varying on-time, where the period is the inverse of the sampling frequency, and the on-time is proportional to the sine-wave signal magnitude, is produced at the output of each comparator. These signals are coupled to the inputs of the pre-output driving stage.

The driving stage may include two high-speed high-side/low-side MOSFET drivers, such as, for example, Micrel MIC4102, for driving each half of the power output stage H-bridge. This circuit makes use of the built-in adaptive dead-time control which frees the microcontroller 100 from having to adjust the dead-time control based on the changing load conditions seen by the output amplifier 130. These MOSFET drivers switch at speeds up to several Megahertz without significant switching losses. Low on-resistance of the internal transistor switching devices also keeps circuit losses to a minimum.

The power output stage may include four independent power switching devices, or two integrated half-bridge power switching devices, in an H-bridge configuration. Each half-bridge is ultimately coupled to the primary side of the power output isolation transformer after first passing through the low pass filter 134.

In one embodiment, the low pass filter 134 includes two independent LC filter networks that are connected between each half H-bridge output of the switching/PWM amplifier 132 and the inputs to the primary side of the signal/isolation transformers 140. One purpose of the LC filter circuits is to reform two sinusoidal driving signals from the switching signals created by the switching amplifier 132. Locating the LC filter circuits before the inputs of the signal/isolation transformers 140 allows lower grade magnetics to be used in the construction of the isolation output transformer, since the transformer will only see signal frequencies in the range of the attached ultrasonic atomizer load, i.e., several tens to hundreds of kilohertz, rather than the higher switching frequencies, i.e., several Megahertz, produced by the switching/PWM amplifier 132. Radio Frequency (RF) radiation is also reduced, since lower frequency sinusoidal waveforms are presented to the signal/isolation transformers 140 rather than the higher-frequency sharper-edged waveforms produced by the output amplifier 130. Switching losses are also reduced within the transformer due to the lower frequencies present.

With respect to the linear amplifier 132', embodiments include at least a differential input stage, a voltage amplifier stage, an output stage and a power amplifier pre-regulator. The power amplifier pre-regulator produces and supplies a variable voltage to the output stage, whose magnitude is set based on the requirements of the attached ultrasonic atomizer load.

The signal/isolation transformers 140 includes the main isolation power transformer, the voltage sense isolation transformer and the current sense isolation transformer circuits.

The main isolation power transformer couples the re-created output signals, generated by the switching/PWM amplifier 132 and low pass filter 134, or by the linear amplifier 132', to the load presented by the ultrasonic atomizer nozzle 1. The main isolation power transformer provides isolation between the internal driving circuits and the ultrasonic atomizer. This isolated output can then be referenced to earth, or another reference voltage, without affecting the internal circuits. The main isolation output transformer also steps-up the output voltage in the ranges required by the ultrasonic atomizer nozzle without requiring high voltage power supplies to supply the output amplifier 130. The main isolation output transformer also provides better load matching between the output amplifier 130 and the load presented by the ultrasonic atomizer nozzle 1. The main isolation output transformer may be constructed with a single winding on the primary and multiple windings on the secondary. The multiple windings may be switched in and out by active circuits, controlled by microcontroller 100, that switch to the proper winding to provide the best load matching between the output amplifier 130 and any low pass filter components associated therewith, and the load presented by the ultrasonic atomizer nozzle 1. The ability to switch between multiple secondary windings also provides optimal output amplifier efficiency through better load matching.

The voltage sense isolation transformer creates a low-level signal from the high-level signal delivered to the ultrasonic atomizer nozzle 1. The low level voltage signal is coupled to the input of a differential input amplifier, such as, for example, Texas Instruments THS4531, whose output is provided to the voltage level detector circuit 170 and the phase detector 180. The voltage sense transformer reduces the output voltage signal to a level compatible with these circuits. Both the primary and secondary may be single winding construction, respectively.

The current sense isolation transformer creates a low-level voltage signal proportional to the high-level current signal delivered to the ultrasonic atomizer nozzle 1. The low level signal is coupled to the input of a differential input amplifier, such as, for example, Texas Instruments THS4531, whose output is used by the current level detector circuit 160 and the phase detector 180. The current sense transformer reduces the output current signal to a level compatible with these circuits. Both the primary and secondary may be single winding construction, respectively.

The current level detector circuit 160 receives half of the differential alternating-current (AC) current signal, generated by the current sense transformer circuit, whose signal is proportional the output current in the ultrasonic atomizer nozzle drive power signal, and converts that signal into a direct-current (DC) voltage proportional to the root-mean-square voltage of the applied A/C signal. An RMS-to-DC converter, such as, for example, Linear Technology LTC1968, is used to convert the signal from the A/C RMS voltage to the proportional DC voltage. The DC voltage produced by the converter is then amplified to match the signal levels of the respective ADC of the microcontroller 100. The microcontroller 100 reads this voltage periodically, typically greater several times per second, and responds accordingly.

The voltage level detector circuit 170 receives half of the differential alternating-current (AC) voltage signal, generated by the voltage sense transformer circuit, whose signal is proportional the output voltage in the ultrasonic atomizer nozzle drive power signal, and converts that signal into a direct-current (DC) voltage proportional to the root-mean-square voltage of the applied A/C signal. An RMS-to-DC converter, such as, for example, Linear Technology LTC1968, is used to convert the signal from the A/C RMS voltage to the proportional DC voltage. The DC voltage produced by the converter is then amplified to match the signal levels of the respective ADC of the microcontroller 100. The microcontroller 100 reads this voltage periodically, typically greater several times per second, and responds accordingly.

The phase detector 180 first receives the full differential signals produced from the voltage sense and current sense transformer circuits. These signals are then supplied to two independent differential comparator circuits which produce a square-wave proportional to the original differential signals. When the voltage and current signals supplied to the ultrasonic atomizer nozzle 1 are in phase with each other, the resultant voltage and current square-waves will be 180° out of phase with each other. The square-waves signals are then de-glitched through Schmitt-trigger inverters, and passed to the input of a phase detector circuit. The output of the phase detector circuit is filtered via a low-pass RC circuit to produce a DC voltage proportional to the phase difference of the voltage and current waveforms. The DC voltage produced by the phase detector 180 is then conditioned to match the signal levels of the respective ADC of the microcontroller 100. The microcontroller 100 reads this voltage periodically, typically greater several times per second, and responds accordingly.

As noted above, the I/O interface 40 may include several digital and analog inputs and outputs. A digital trigger input, a digital alarm output and a ultrasonic atomizer nozzle power/load level control analog input are provided. Additional inputs and outputs include at least one digital input, one digital output, one analog input, and one analog output for controlling spray processing components other than the ultrasonic atomizing nozzle 1.

The digital inputs may be high-speed optically isolated inputs that provide galvanic signal isolation while also providing fast response. In one embodiment, Vishay SFH6286-3T opto-coupler devices are used to provide high-speed optical isolation between the applied external control signal and the on-board circuits.

The digital outputs may be optically isolated high-speed circuits that allow connection to various output loads, such as, but not limited to, solenoids, proportional valves, motors and pumps. In one embodiment, an open-drain circuit, including a Toshiba TLP701 high-speed opto-coupler coupled to a Fairchild Semiconductor FQT7N10LTF N-Channel MOSFET, is used to allow maximum compatibility with the many possible load types and to provide signal isolation between the driving signal and the load. Provision for supplying circuit power from an external power source is provided to further promote circuit isolation and promote the greatest connectivity to the multiple load types. The digital outputs may be configured to operate in a time-varying manner, such as pulse-width-modulation, to drive the attached load in a variable manner, such as required by, but not limited to, proportional valves, pumps and motors. The digital outputs can also be configured for digital on/off operation for loads that only require a digital on/off signal.

The analog inputs may be configurable to accept input voltages from, but not limited to, 0-5 VDC or 0-10 VDC. The analog input circuits may include current and voltage limiting components to prevent over-current and over-voltage events from destroying the associated analog input circuits. In one embodiment, Texas Instrument's TLV2372 operational amplifiers are used as the main conditioning element between the incoming signal and the on-board circuits.

The analog outputs may generate output voltages in, but not limited to, the 0-5 VDC or 0-10 VDC ranges. The dual range of these outputs allows greatest connectivity and compatibility with the various devices that will utilize these output signals. Devices include pumps, pressure regulators, flow regulators and other process control devices. In one embodiment, a Microchip MCP4726A1T digital-to-analog converter generates raw, un-conditioned voltage, which is then amplified to the appropriate level via a Texas Instruments TLV2372 operational amplifier. The use of the operational amplifier also provides greater output current drive capability, over the MCP4726 digital-to-analog converter device, increasing the number of devices that can be driven by the output.

The microcontroller 100 provides at least one user-selectable operating mode, including a load leveling operating mode. In some embodiments, the microcontroller 100 also provides a power leveling mode.

In the load leveling operating mode, the microcontroller 100 controls the output power of the output amplifier 130 to match changes in the load condition of the ultrasonic atomizing nozzle 1, which occur, for example, when liquid is introduced to the atomizer, when the liquid itself suddenly changes in flow rate, viscosity, or concentration, etc. In other words, microcontroller 100 adaptively reacts to changes in the load of the ultrasonic atomizing nozzle 1 in order to ensure that the real amplifier output power is commensurate with the nozzle load. For example, assuming the general relationship $P=I^2\times R$, for a fixed current, as resistance increases, power increases, as given in Equation 1 below.

$$P\uparrow = \overleftrightarrow{I}^2 \times R\uparrow$$

Figure 6A:
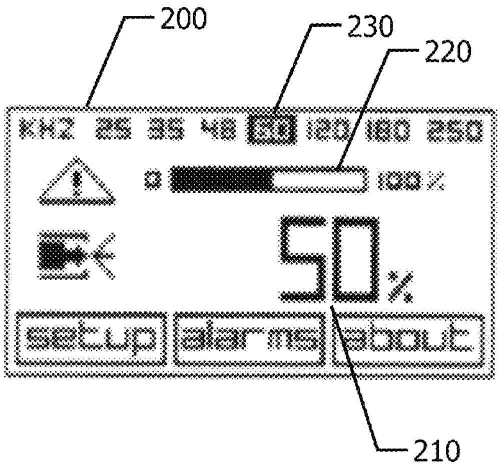
FIGS. 6A and 6B depict a graphical user interface screen for a dynamic ultrasonic generator display, in accordance with an embodiment of the present invention.

The user selects a load leveling set-point as a percentage of maximum load leveling capability, which is presented on display 20. FIG. 6A depicts a graphical user interface screen 200, for presentation on display 20, for load leveling operating mode for a 50% load leveling set-point, depicting the load leveling set-point 210, the percentage of maximum load leveling capability 220, and the nozzle frequency 230.

More particularly, the microcontroller 100 determines an optimal frequency and operates at that optimal frequency, while still maintaining a phase relationship between the driving signal voltage and current components at, or other than, a 0° phase relationship. In one embodiment, to be compatible with different nozzle loads and ranges of frequencies, the microcontroller 100 analyzes the state of the ultrasonic atomizing nozzle 1 and automatically switches between multiple taps on a secondary side of an output transformer device. As such, maximum load matching to the output amplifier 130, increased overall amplifier efficiency, and higher optimization of filter components integral to the output amplifier 130 can be advantageously achieved.

Figure 7A:
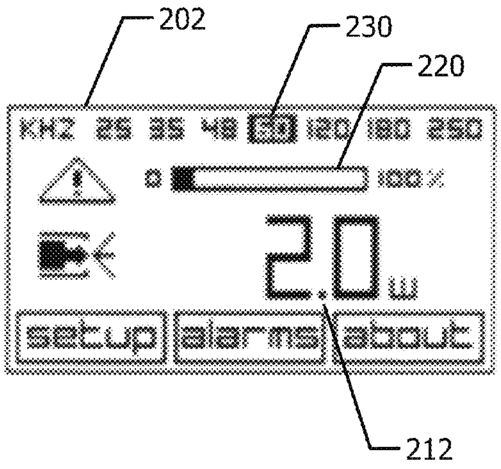
FIGS. 7A and 7B depict a graphical user interface screen for a dynamic ultrasonic generator display, in accordance with an embodiment of the present invention.

In the power leveling operating mode, the microcontroller 100 controls the output power of the output amplifier 130 to a fixed, power-set point selected by the user for any nozzle load, which is presented on display 20. FIG. 7A depicts a graphical user interface screen 202, for presentation on display 20, for power leveling operating mode for a 2.0 W power set-point, depicting the power set-point 212, the percentage of maximum power 220, and the nozzle frequency 230.

Using the dynamic ultrasonic generator 10, an ultrasonic atomizer nozzle 1 may be used to atomize a normally viscous liquid that only atomizes when it is heated to an optimal elevated temperature. In one embodiment, the microcontroller 100 is coupled to the controllable fluid source (not shown), via I/O interface 40, serial interface 50, Ethernet interface 60, etc., and controls the flow of fluid to the ultrasonic atomizing nozzle 1, which is fluidly coupled to an output port of the fluid source. The microcontroller 100 stops the liquid flow by sending a command to the fluid source, and then operates the ultrasonic atomizer nozzle 1 at a reference power level for a predetermined or user-selectable period of time in order to heat the ultrasonic atomizer nozzle 1 to a temperature suitable for atomization. Once a suitable temperature is reached, microcontroller 100 resumes the flow of liquid by sending a command to the fluid source.

Microcontroller 100 may elevate, or spike, the power set point for a short period of time when first triggered, to start the atomizing process, and then revert the power set point to the standard operating power specific to the atomizing process. The user can select the spike power set point and duration for both load leveling mode and for power leveling mode.

Another atomizing process improvement includes spraying evolutions that are only milliseconds long in their entire duration. Typically, applications requiring fine amounts of material deposition also require process speed considerations. Such high-speed atomizing evolutions have time periods shorter than the time necessary for current control systems to level-out when a spray trigger is applied. Therefore, the microcontroller 100 advantageously keeps the atomizer frequency continually locked by driving the ultrasonic atomizing nozzle 1 at extremely low, idle power levels, such that atomization doesn't occur, but allows the frequency and driving signal control functions to stay initialized for quick response. Then, at the moment of the spray evolution, the power is increased from the idle power level to the normal atomization level. As such, start stop times of several hundred milliseconds can be reduced to tens of milliseconds, depending on the particular application. The user can select the idle set-points for both load leveling mode and for power leveling mode.

Figure 6B:
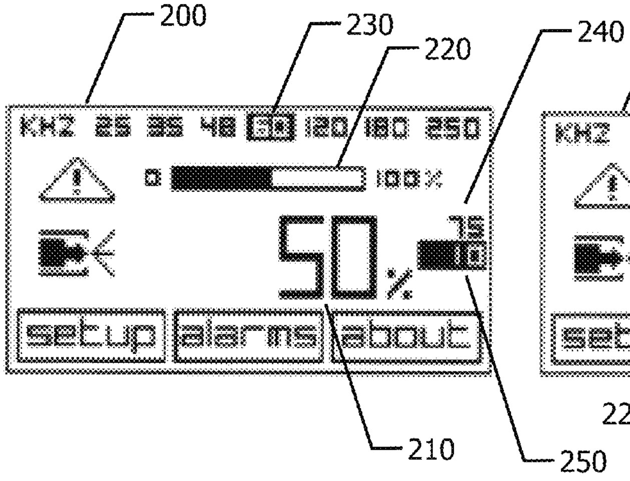
Figure 7B:
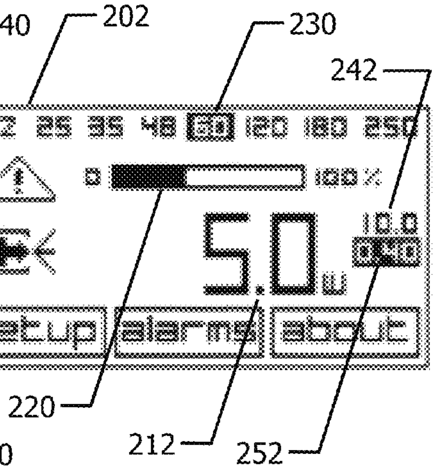

FIG. 6B depicts a graphical user interface screen 200, for presentation on display 20, for load leveling operating mode for a 50% load leveling set-point, a 75% spike set-point and a 10% idle set-point, depicting the load leveling set-point 210, the percentage of maximum load leveling capability 220, the nozzle frequency 230, the spike set-point 240 and the idle set-point 250. FIG. 7B depicts a graphical user interface screen 202, for presentation on display 20, for power leveling operating mode for a 2.0 W power set-point, a 10.0 W spike set-point and a 0.4 W idle set-point, depicting the power set-point 212, the percentage of maximum power 220, the nozzle frequency 230, the spike set-point 242 and the idle set-point 252.

The many features and advantages of the invention are apparent from the detailed specification, and, thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and, accordingly, all suitable modifications and equivalents may be resorted to that fall within the scope of the invention.

What is claimed is:

1. An ultrasonic generator, comprising:

an amplifier for outputting a drive signal to an ultrasonic atomizing nozzle; and a microcontroller, coupled to the amplifier, to control an output power of the amplifier, wherein the microcontroller includes a load leveling operating mode which controls the output power of the amplifier by monitoring and compensating for changes in impedance of the ultrasonic atomizing nozzle.

2. The ultrasonic generator according to claim 1, wherein the microcontroller includes a power leveling operating mode which controls the output power of the amplifier to a fixed set-point during changes in impedance of the ultrasonic atomizing nozzle.

3. The ultrasonic generator according to claim 1, wherein the amplifier is a switching amplifier coupled to a low-pass filter.

4. The ultrasonic generator according to claim 1, wherein the amplifier is a linear amplifier.

5. The ultrasonic generator according to claim 1, further comprising:

a plurality of isolation transformers, coupled to the amplifier and the ultrasonic atomizing nozzle, to output a voltage sense signal and a current sense signal based on the drive signal; and a digital phase detection circuit, coupled to the isolation transformers and the microcontroller, to output a phase difference signal, based on the voltage and current sense signals, to the microcontroller, wherein the microcontroller is configured to lock onto a resonant frequency of the ultrasonic atomizer nozzle based on the phase difference signal.

6. The ultrasonic generator according to claim 1, wherein the microcontroller sets the voltage and current components of the drive signal up to +/−60° out-of-phase.

7. The ultrasonic generator according to claim 5, wherein the microcontroller sets the voltage and current components of the drive signal up to +/−60° out-of-phase.

8. The ultrasonic generator according to claim 5, wherein one of the transformers has multiple taps on a secondary-side that are automatically switched in and out by the microcontroller based on calculated real-time impedance of the ultrasonic atomizer nozzle, and wherein the microcontroller optimally matches the impedance between the amplifier and any associated low pass filter components, and the ultrasonic atomizer nozzle.

9. The ultrasonic generator according to claim 8, wherein the operating efficiency of the amplifier increases due to the optimal impedance matching.

10. The ultrasonic generator according to claim 1, further comprising a plurality of digital and analog inputs and outputs, coupled to the microcontroller, to communicate with liquid and gas flow equipment.

11. The ultrasonic generator according to claim 10, wherein the microcontroller controls the amplifier power to keep liquids warm inside the ultrasonic atomizing nozzle when a trigger signal is removed from one of the analog or digital inputs.

12. The ultrasonic generator according to claim 1, further comprising a temperature sense circuit, coupled to the microcontroller and a temperature sensor attached to the ultrasonic atomizing nozzle, for monitoring the temperature of the ultrasonic atomizing nozzle, wherein the microcontroller controls the amplifier output power to control the temperature of the ultrasonic atomizing nozzle.

13. The ultrasonic generator according to claim 12, wherein the microcontroller reduces the amplifier output power to avoid an over-temperature condition of the ultrasonic atomizing nozzle.

14. The ultrasonic generator according to claim 12, wherein the microcontroller generates at least one of an alarm condition, a user notification, or activates an alarm output when an over-temperature condition of the ultrasonic atomizing nozzle is detected.

15. The ultrasonic generator according to claim 12, wherein the microcontroller automatically removes the driving signal to the ultrasonic atomizing nozzle when a critical over-temperature is reached.

16. The ultrasonic generator according to claim 10, wherein the microcontroller elevates the amplifier output power, from a nominal power level to a predetermined power level, for a predetermined period of time after a trigger event, and wherein the microcontroller reduces the amplifier output power, from the predetermined power level to the nominal level, after the predetermined period of time elapses.

17. The ultrasonic generator according to claim 10, wherein the microcontroller starts and stops fluid atomization by the ultrasonic atomizing nozzle when an external trigger signal is applied and removed, respectively, from a digital or analog input, and wherein the microcontroller maintains an idle power to the ultrasonic atomization nozzle during the stop cycle.

18. An ultrasonic spraying system, comprising:

a fluid source including a controllable output port;

an ultrasonic atomizing nozzle, coupled to the fluid source, including at least one piezoelectric transducer coupled to a fluid atomizing horn; and an ultrasonic generator, coupled to the fluid source and the ultrasonic atomizing nozzle, including:

at least one communications port, a nozzle drive signal output port, an amplifier, coupled to the nozzle drive signal output port, and a microcontroller, coupled to the communications port and the amplifier, to control the fluid source and to control an output power of the amplifier, the microcontroller including a load leveling operating mode which controls the output power of the amplifier by monitoring and compensating for changes in impedance of the ultrasonic atomizing nozzle.

19. The system according to claim 18, wherein the microcontroller elevates the amplifier output power, from a nominal power level to a predetermined power level, for a predetermined period of time after a trigger event, and wherein the microcontroller reduces the amplifier output power, from the predetermined power level to the nominal level, after the predetermined period of time elapses.

20. The system according to claim 18, wherein the microcontroller starts and stops fluid atomization by the ultrasonic atomizing nozzle when an external trigger signal is applied and removed, respectively, from the communications port, and wherein the microcontroller maintains an idle power to the ultrasonic atomization nozzle during the stop cycle.

21. The system according to claim 18, wherein the microcontroller includes a power leveling operating mode which controls the output power of the amplifier to a fixed set-point during changes in impedance of the ultrasonic atomizing nozzle.

* * * * *